(12) United States Patent
Stone et al.

(10) Patent No.: US 8,864,769 B2
(45) Date of Patent: Oct. 21, 2014

(54) ALIGNMENT GUIDES WITH PATIENT-SPECIFIC ANCHORING ELEMENTS

(75) Inventors: Kevin T. Stone, Winona Lake, IN (US); Thomas J. Mauch, South Bend, IN (US); Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 338 days.

(21) Appl. No.: 13/041,495

(22) Filed: Mar. 7, 2011

(65) Prior Publication Data

US 2011/0166578 A1 Jul. 7, 2011

Related U.S. Application Data

(63) Continuation-in-part of application No. 12/973,214, filed on Dec. 20, 2010, which is a continuation-in-part of application No. 12/955,361, filed on Nov. 29, 2010, now Pat. No. 8,591,516, which is a continuation-in-part of application No. 12/938,905, filed on Nov. 3, 2010, and a continuation-in-part of application No. 12/938,913, filed on Nov. 3, 2010, said application No. 12/938,905 is a continuation-in-part of application No. 12/893,306, filed on Sep. 29, 2010, said application No. 12/938,913 is a continuation-in-part of application No. 12/893,306, which is a continuation-in-part of application No. 12/888,005, filed on Sep. 22, 2010, now Pat. No. 8,377,066, which is a continuation-in-part of application No. 12/714,023, filed on Feb. 26, 2010, now Pat. No. 8,241,293, which is a continuation-in-part of application No. 12/571,969, filed on Oct. 1, 2009, which is a continuation-in-part of application No. 12/486,992, filed on Jun. 18, 2009, and a continuation-in-part of application No. 12/389,901, filed on Feb. 20, 2009, now Pat. No. 8,133,234, which is a continuation-in-part of application No. 12/211,407, filed on Sep. 16, 2008, now Pat. No. 8,608,748, which is a continuation-in-part of application No. 12/039,849, filed on Feb. 29, 2008, now Pat. No. 8,282,646, which is a (Continued)

(51) Int. Cl.
*A61B 17/56* (2006.01)
*A61B 17/15* (2006.01)
*A61B 19/00* (2006.01)

(52) U.S. Cl.
CPC ......... *A61B 17/151* (2013.01); *A61B 2019/508* (2013.01); *A61B 19/50* (2013.01); *A61B 17/152* (2013.01); *A61B 2019/505* (2013.01)
USPC .......................................................... 606/88

(58) Field of Classification Search
CPC .. A61B 1/00; A61B 2010/00; A61B 2217/00; A61B 2218/00; A61F 2/00
USPC ........................ 623/21.11–21.16; 606/61, 87
See application file for complete search history.

(56) References Cited

U.S. PATENT DOCUMENTS

| | | |
|---|---|---|
| 1,480,285 A | 1/1924 | Moore |
| 2,181,746 A | 11/1939 | Siebrandt |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

International Preliminary Report on Patentability for PCT/US2010/050701 mailed Apr. 12, 2012 claiming benefit of U.S. Appl. No. 12/571,969, filed Oct. 1, 2009.

(Continued)

*Primary Examiner* — David Isabella
*Assistant Examiner* — Ann Schillinger
(74) *Attorney, Agent, or Firm* — Harness, Dickey

(57) ABSTRACT

An orthopedic device for joint arthroplasty includes an alignment guide and a number of patient-specific anchoring elements. The alignment guide can be mounted on a bone of a patient during joint arthroplasty. The patient-specific anchoring elements extend from an inner surface of the alignment guide and have a patient-specific length relative to an outer bone surface of the bone of the patient.

28 Claims, 6 Drawing Sheets

Related U.S. Application Data continuation-in-part of application No. 11/756,057, filed on May 31, 2007, now Pat. No. 8,092,465, and a continuation-in-part of application No. 11/971,390, filed on Jan. 9, 2008, now Pat. No. 8,070,752, which is a continuation-in-part of application No. 11/363,548, filed on Feb. 27, 2006, now Pat. No. 7,780,672, said application No. 12/039,849 is a continuation-in-part of application No. 12/025,414, filed on Feb. 4, 2008, now Pat. No. 8,298,237, application No. 13/041,495, which is a continuation-in-part of application No. 12/872,663, filed on Aug. 31, 2010, now Pat. No. 8,407,067, and a continuation-in-part of application No. 12/483,807, filed on Jun. 12, 2009, now Pat. No. 8,473,305, which is a continuation-in-part of application No. 12/371,096, filed on Feb. 13, 2009, which is a continuation-in-part of application No. 12/103,824, filed on Apr. 16, 2008, now abandoned, application No. 13/041,495, which is a continuation-in-part of application No. 12/103,834, filed on Apr. 16, 2008, now Pat. No. 7,967,868, and a continuation-in-part of application No. 12/978,069, filed on Dec. 23, 2010, now Pat. No. 8,568,487, which is a continuation-in-part of application No. 12/973,214, filed on Dec. 20, 2010.

(60) Provisional application No. 61/446,660, filed on Feb. 25, 2011, provisional application No. 60/953,620, filed on Aug. 2, 2007, provisional application No. 60/947,813, filed on Jul. 3, 2007, provisional application No. 60/911,297, filed on Apr. 12, 2007, provisional application No. 60/892,349, filed on Mar. 1, 2007, provisional application No. 60/812,694, filed on Jun. 9, 2006, provisional application No. 60/953,637, filed on Aug. 2, 2007, provisional application No. 61/310,752, filed on Mar. 5, 2010, provisional application No. 60/912,178, filed on Apr. 17, 2007.

(56) References Cited

U.S. PATENT DOCUMENTS

| | | | |
|---|---|---|---|
| 2,407,845 | A | 9/1946 | Nemeyer |
| 2,416,228 | A | 2/1947 | Sheppard |
| 2,618,913 | A | 11/1952 | Plancon et al. |
| 2,910,978 | A | 11/1959 | Urist |
| 3,840,904 | A | 10/1974 | Tronzo |
| 4,246,895 | A | 1/1981 | Rehder |
| 4,306,866 | A | 12/1981 | Weissman |
| 4,324,006 | A | 4/1982 | Charnley |
| 4,421,112 | A | 12/1983 | Mains et al. |
| 4,436,684 | A | 3/1984 | White |
| 4,457,306 | A | 7/1984 | Borzone |
| 4,475,549 | A | 10/1984 | Oh |
| 4,506,393 | A | 3/1985 | Murphy |
| 4,524,766 | A | 6/1985 | Petersen |
| 4,528,980 | A | 7/1985 | Kenna |
| 4,619,658 | A | 10/1986 | Pappas et al. |
| 4,621,630 | A | 11/1986 | Kenna |
| 4,632,111 | A | 12/1986 | Roche |
| 4,633,862 | A | 1/1987 | Petersen |
| 4,663,720 | A | 5/1987 | Duret et al. |
| 4,689,984 | A | 9/1987 | Kellner |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,706,660 | A | 11/1987 | Petersen |
| 4,719,907 | A | 1/1988 | Banko et al. |
| 4,721,104 | A | 1/1988 | Kaufman et al. |
| 4,722,330 | A | 2/1988 | Russell et al. |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A | 1/1990 | Vandewalls |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A | 4/1991 | Woolson |
| 5,030,221 | A | 7/1991 | Buechel et al. |
| 5,041,117 | A | 8/1991 | Engelhardt |
| 5,053,037 | A | 10/1991 | Lackey |
| 5,053,039 | A | 10/1991 | Hofmann et al. |
| 5,056,351 | A | 10/1991 | Stiver et al. |
| 5,086,401 | A | 2/1992 | Glassman et al. |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A | 6/1992 | Bert et al. |
| 5,129,908 | A | 7/1992 | Petersen |
| 5,129,909 | A | 7/1992 | Sutherland |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,194,066 | A | 3/1993 | Van Zile |
| 5,246,444 | A | 9/1993 | Schreiber |
| 5,253,506 | A | 10/1993 | Davis et al. |
| 5,258,032 | A | 11/1993 | Bertin |
| 5,261,915 | A | 11/1993 | Durlacher et al. |
| 5,274,565 | A | 12/1993 | Reuben |
| 5,299,288 | A | 3/1994 | Glassman et al. |
| 5,300,077 | A | 4/1994 | Howell |
| 5,320,529 | A | 6/1994 | Pompa |
| 5,320,625 | A | 6/1994 | Bertin |
| 5,323,697 | A | 6/1994 | Schrock |
| 5,342,366 | A | 8/1994 | Whiteside et al. |
| 5,344,423 | A | 9/1994 | Dietz et al. |
| 5,360,446 | A | 11/1994 | Kennedy |
| 5,364,402 | A | 11/1994 | Mumme et al. |
| 5,368,858 | A | 11/1994 | Hunziker |
| 5,370,692 | A | 12/1994 | Fink et al. |
| 5,370,699 | A | 12/1994 | Hood et al. |
| 5,405,395 | A | 4/1995 | Coates |
| 5,408,409 | A | 4/1995 | Glassman et al. |
| 5,411,521 | A | 5/1995 | Putnam et al. |
| 5,415,662 | A | 5/1995 | Ferrante et al. |
| 5,417,694 | A | 5/1995 | Marik et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |
| 5,472,415 | A | 12/1995 | King et al. |
| 5,474,559 | A | 12/1995 | Bertin et al. |
| 5,490,854 | A | 2/1996 | Fisher et al. |
| 5,496,324 | A | 3/1996 | Barnes |
| 5,507,833 | A | 4/1996 | Bohn |
| 5,514,519 | A | 5/1996 | Neckers |
| 5,520,695 | A | 5/1996 | Luckman |
| 5,527,317 | A | 6/1996 | Ashby et al. |
| 5,539,649 | A | 7/1996 | Walsh et al. |
| 5,540,695 | A | 7/1996 | Levy |
| 5,545,222 | A | 8/1996 | Bonutti |
| 5,549,688 | A | 8/1996 | Ries et al. |
| 5,554,190 | A | 9/1996 | Draenert |
| 5,560,096 | A | 10/1996 | Stephens |
| 5,571,110 | A | 11/1996 | Matsen, III et al. |

(56) References Cited

U.S. PATENT DOCUMENTS

| | | | |
|---|---|---|---|
| 5,578,037 | A | 11/1996 | Sanders et al. |
| 5,595,703 | A | 1/1997 | Swaelens et al. |
| 5,607,431 | A | 3/1997 | Dudasik et al. |
| 5,613,969 | A | 3/1997 | Jenkins, Jr. |
| 5,620,448 | A | 4/1997 | Puddu |
| 5,634,927 | A | 6/1997 | Houston et al. |
| 5,641,323 | A | 6/1997 | Caldarise |
| 5,658,294 | A | 8/1997 | Sederholm |
| 5,662,656 | A | 9/1997 | White |
| 5,662,710 | A | 9/1997 | Bonutti |
| 5,671,018 | A | 9/1997 | Ohara et al. |
| 5,677,107 | A | 10/1997 | Neckers |
| 5,681,354 | A | 10/1997 | Eckhoff |
| 5,682,886 | A | 11/1997 | Delp et al. |
| 5,683,469 | A | 11/1997 | Johnson et al. |
| 5,690,635 | A | 11/1997 | Matsen, III et al. |
| 5,697,933 | A | 12/1997 | Gundlapalli et al. |
| 5,702,460 | A | 12/1997 | Carls et al. |
| 5,702,464 | A | 12/1997 | Lackey et al. |
| 5,704,941 | A | 1/1998 | Jacober et al. |
| 5,722,978 | A | 3/1998 | Jenkins, Jr. |
| 5,725,376 | A | 3/1998 | Poirier |
| 5,725,593 | A | 3/1998 | Caracciolo |
| 5,735,277 | A | 4/1998 | Schuster |
| 5,748,767 | A | 5/1998 | Raab |
| 5,749,875 | A | 5/1998 | Puddu |
| 5,749,876 | A | 5/1998 | Duvillier et al. |
| 5,762,125 | A | 6/1998 | Mastrorio |
| 5,768,134 | A | 6/1998 | Swaelens et al. |
| 5,769,092 | A | 6/1998 | Williamson, Jr. |
| 5,776,200 | A | 7/1998 | Johnson et al. |
| 5,786,217 | A | 7/1998 | Tubo et al. |
| 5,792,143 | A | 8/1998 | Samuelson et al. |
| 5,798,924 | A | 8/1998 | Eufinger et al. |
| 5,799,055 | A | 8/1998 | Peshkin et al. |
| 5,860,980 | A | 1/1999 | Axelson, Jr. et al. |
| 5,860,981 | A | 1/1999 | Bertin et al. |
| 5,871,018 | A | 2/1999 | Delp et al. |
| 5,876,456 | A | 3/1999 | Sederholm et al. |
| 5,879,398 | A | 3/1999 | Swarts et al. |
| 5,879,402 | A | 3/1999 | Lawes et al. |
| 5,880,976 | A | 3/1999 | DiGioia, III et al. |
| 5,885,297 | A | 3/1999 | Matsen, III |
| 5,885,298 | A | 3/1999 | Herrington et al. |
| 5,888,219 | A | 3/1999 | Bonutti |
| 5,895,389 | A | 4/1999 | Schenk et al. |
| 5,899,907 | A | 5/1999 | Johnson |
| 5,901,060 | A | 5/1999 | Schall et al. |
| 5,911,724 | A | 6/1999 | Wehrli |
| 5,921,988 | A | 7/1999 | Legrand |
| 5,925,049 | A | 7/1999 | Gustilo et al. |
| 5,942,370 | A | 8/1999 | Neckers |
| 5,967,777 | A | 10/1999 | Klein et al. |
| 5,976,149 | A | 11/1999 | Masini |
| 5,980,526 | A | 11/1999 | Johnson et al. |
| 6,033,415 | A | 3/2000 | Mittelstadt et al. |
| 6,059,789 | A * | 5/2000 | Dinger et al. .............. 606/96 |
| 6,059,833 | A | 5/2000 | Doets |
| 6,086,593 | A | 7/2000 | Bonutti |
| 6,120,510 | A | 9/2000 | Albrektsson et al. |
| 6,120,544 | A | 9/2000 | Grundei et al. |
| 6,126,690 | A | 10/2000 | Ateshian et al. |
| 6,126,692 | A | 10/2000 | Robie et al. |
| 6,136,033 | A | 10/2000 | Suemer |
| 6,156,069 | A | 12/2000 | Amstutz |
| 6,159,217 | A * | 12/2000 | Robie et al. .............. 606/88 |
| 6,161,080 | A | 12/2000 | Aouni-Ateshian et al. |
| 6,162,257 | A | 12/2000 | Gustilo et al. |
| 6,187,010 | B1 | 2/2001 | Masini |
| 6,195,615 | B1 | 2/2001 | Lysen |
| 6,203,546 | B1 | 3/2001 | MacMahon |
| 6,205,411 | B1 | 3/2001 | DiGioia, III et al. |
| 6,206,927 | B1 | 3/2001 | Fell et al. |
| 6,238,435 | B1 | 5/2001 | Meulink et al. |
| 6,254,604 | B1 | 7/2001 | Howell |
| 6,258,097 | B1 | 7/2001 | Cook et al. |
| 6,264,698 | B1 | 7/2001 | Lawes et al. |
| 6,270,529 | B1 | 8/2001 | Terrill-Grisoni et al. |
| 6,273,891 | B1 | 8/2001 | Masini |
| 6,290,727 | B1 | 9/2001 | Otto et al. |
| 6,293,971 | B1 | 9/2001 | Nelson et al. |
| 6,310,269 | B1 | 10/2001 | Friese et al. |
| 6,312,258 | B1 | 11/2001 | Ashman |
| 6,312,473 | B1 | 11/2001 | Oshida |
| 6,319,285 | B1 | 11/2001 | Chamier et al. |
| 6,325,829 | B1 | 12/2001 | Schmotzer |
| 6,338,738 | B1 | 1/2002 | Bellotti et al. |
| 6,343,987 | B2 | 2/2002 | Hayama et al. |
| 6,354,011 | B1 | 3/2002 | Albrecht |
| 6,361,563 | B2 | 3/2002 | Terrill-Grisoni et al. |
| 6,379,299 | B1 | 4/2002 | Borodulin et al. |
| 6,379,388 | B1 | 4/2002 | Ensign et al. |
| 6,383,228 | B1 | 5/2002 | Schmotzer |
| 6,391,251 | B1 | 5/2002 | Keicher et al. |
| 6,395,005 | B1 | 5/2002 | Lovell |
| 6,424,332 | B1 | 7/2002 | Powell |
| 6,427,698 | B1 | 8/2002 | Yoon |
| 6,459,948 | B1 | 10/2002 | Ateshian et al. |
| 6,463,351 | B1 | 10/2002 | Clynch |
| 6,475,243 | B1 | 11/2002 | Sheldon et al. |
| 6,482,236 | B2 * | 11/2002 | Habecker .............. 623/18.11 |
| 6,488,715 | B1 | 12/2002 | Pope et al. |
| 6,503,255 | B1 | 1/2003 | Albrektsson et al. |
| 6,510,334 | B1 | 1/2003 | Schuster et al. |
| 6,514,259 | B2 | 2/2003 | Picard et al. |
| 6,517,583 | B1 | 2/2003 | Pope et al. |
| 6,519,998 | B2 | 2/2003 | Ertl et al. |
| 6,520,964 | B2 | 2/2003 | Tallarida et al. |
| 6,533,737 | B1 | 3/2003 | Brosseau et al. |
| 6,547,823 | B2 | 4/2003 | Scarborough et al. |
| 6,554,837 | B1 | 4/2003 | Hauri et al. |
| 6,556,008 | B2 | 4/2003 | Thesen |
| 6,558,391 | B2 | 5/2003 | Axelson, Jr. et al. |
| 6,558,428 | B2 | 5/2003 | Park |
| 6,564,085 | B2 | 5/2003 | Meaney et al. |
| 6,567,681 | B1 | 5/2003 | Lindequist |
| 6,575,980 | B1 | 6/2003 | Robie et al. |
| 6,575,982 | B1 | 6/2003 | Bonutti |
| 6,591,581 | B2 | 7/2003 | Schmieding |
| 6,605,293 | B1 | 8/2003 | Giordano et al. |
| 6,622,567 | B1 | 9/2003 | Hamel et al. |
| 6,629,999 | B1 | 10/2003 | Serafin, Jr. |
| 6,641,617 | B1 | 11/2003 | Merrill et al. |
| 6,682,566 | B2 | 1/2004 | Draenert |
| 6,696,073 | B2 | 2/2004 | Boyce et al. |
| 6,697,664 | B2 | 2/2004 | Kienzle, III et al. |
| 6,701,174 | B1 | 3/2004 | Krause et al. |
| 6,709,462 | B2 | 3/2004 | Hanssen |
| 6,711,431 | B2 | 3/2004 | Sarin et al. |
| 6,711,432 | B1 | 3/2004 | Krause et al. |
| 6,712,856 | B1 | 3/2004 | Carignan et al. |
| 6,716,249 | B2 | 4/2004 | Hyde |
| 6,725,077 | B1 | 4/2004 | Balloni et al. |
| 6,738,657 | B1 | 5/2004 | Franklin et al. |
| 6,740,092 | B2 | 5/2004 | Lombardo et al. |
| 6,749,638 | B1 | 6/2004 | Saladino |
| 6,750,653 | B1 | 6/2004 | Zou et al. |
| 6,772,026 | B2 | 8/2004 | Bradbury et al. |
| 6,780,190 | B2 | 8/2004 | Maroney |
| 6,786,930 | B2 | 9/2004 | Biscup |
| 6,799,066 | B2 | 9/2004 | Steines et al. |
| 6,823,871 | B2 | 11/2004 | Schmieding |
| 6,827,723 | B2 | 12/2004 | Carson |
| 6,887,247 | B1 | 5/2005 | Couture et al. |
| 6,905,514 | B2 | 6/2005 | Carignan et al. |
| 6,923,817 | B2 | 8/2005 | Carson et al. |
| 6,923,831 | B2 | 8/2005 | Fell et al. |
| 6,932,842 | B1 | 8/2005 | Litschko et al. |
| 6,942,475 | B2 | 9/2005 | Ensign et al. |
| 6,944,518 | B2 | 9/2005 | Roose |
| 6,945,976 | B2 | 9/2005 | Ball et al. |
| 6,953,480 | B2 | 10/2005 | Mears et al. |
| 6,960,216 | B2 | 11/2005 | Kolb et al. |
| 6,990,220 | B2 | 1/2006 | Ellis et al. |

(56) References Cited

U.S. PATENT DOCUMENTS

| | | |
|---|---|---|
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Buttler et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,211,112 B2 | 7/2012 | Novak et al. |
| 8,241,292 B2 | 8/2012 | Collazo |
| 8,241,293 B2 | 8/2012 | Stone et al. |
| 8,265,790 B2 | 9/2012 | Amiot et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaβky et al. |
| D672,038 S | 12/2012 | Frey |
| 8,333,772 B2 | 12/2012 | Fox et al. |
| 8,355,773 B2 | 1/2013 | Leitner et al. |
| 8,377,066 B2 | 2/2013 | Katrana et al. |
| 8,398,646 B2 | 3/2013 | Metzger et al. |
| 8,407,067 B2 | 3/2013 | Uthgenannt et al. |
| 8,439,675 B2 | 5/2013 | De Moyer |
| 8,439,925 B2 | 5/2013 | Marino et al. |
| 8,473,305 B2 | 6/2013 | Belcher et al. |
| 8,486,150 B2 | 7/2013 | White et al. |
| 8,532,807 B2 | 9/2013 | Metzger |
| 8,535,387 B2 | 9/2013 | Meridew et al. |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,749 B2 | 12/2013 | Meridew et al. |
| 8,632,547 B2 | 1/2014 | Maxson et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0193797 A1 | 12/2002 | Johnson et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |

(56) References Cited

U.S. PATENT DOCUMENTS

| | | |
|---|---|---|
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A2 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1* | 6/2006 | Bennett et al. .................. 606/87 |
| 2006/0136058 A1 | 6/2006 | Pietrzak |
| 2006/0142657 A1 | 6/2006 | Quaid et al. |
| 2006/0149283 A1 | 7/2006 | May et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |

(56) References Cited

U.S. PATENT DOCUMENTS

| | | |
|---|---|---|
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1* | 4/2009 | Aram et al. ............... 606/87 |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |

(56) References Cited

U.S. PATENT DOCUMENTS

| | | |
|---|---|---|
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0022049 A1 | 1/2011 | Huebner et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0172672 A1 | 7/2011 | Dubeau et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-Scoma |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0295887 A1 | 12/2011 | Palmese et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0041445 A1 | 2/2012 | Roose et al. |
| 2012/0065640 A1 | 3/2012 | Metzger et al. |
| 2012/0078254 A1 | 3/2012 | Ashby et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0209276 A1 | 8/2012 | Schuster |
| 2012/0215225 A1 | 8/2012 | Philippon et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |
| 2012/0271314 A1 | 10/2012 | Stemniski et al. |
| 2012/0271366 A1 | 10/2012 | Katrana et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2013/0001121 A1 | 1/2013 | Metzger |
| 2013/0006250 A1 | 1/2013 | Metzger et al. |
| 2013/0035766 A1 | 2/2013 | Meridew |
| 2013/0085500 A1 | 4/2013 | Meridew et al. |
| 2013/0123850 A1 | 5/2013 | Schoenefeld et al. |
| 2013/0197528 A1 | 8/2013 | Zakaria et al. |
| 2013/0218163 A1 | 8/2013 | Frey |
| 2013/0338673 A1 | 12/2013 | Keppler |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |

(56) References Cited

FOREIGN PATENT DOCUMENTS

| | | |
|---|---|---|
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A2 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing

(56) References Cited

OTHER PUBLICATIONS

Specialist® 2 Instrumentation," brochure. (2008) DePuy Orthopaedics, Inc. pp. 1-23.
"Discovery® Elbow System Surgical Technique," brochure. Biomet Orthopedics, Inc. (2008) pp. 1-25.
"Discovery® Elbow System," brochure. Biomet Orthopedics, Inc. (2007) 3 sheets.
"Hipsextant Instructions of Use." (2011) Surgical Planning Associates, Inc. 19 pages.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (2003) pp. 1-8 (12 sheets).
"Patient Matched PMI Implants, C.A.M.R.A. 3-D Imaging," brochure, Biomet, Inc. (1990) 6 pages.
"Regenerex® Tibial Cone Augment, Surgical Technique Addendum to the Vanguard® SSK Revision System," brochure. Biomet® Orthopedics. (2009) pp. 1-8 (12 sheets).
"Signature™ Personalized Patient Care, Surgical Technique Addendum to the Vanguard Knee System" brochure. Biomet® Orthopedics, Inc. (2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (2010) pp. 1-25.
"Zimmer® UniSpacer® Knee System," brochure. (2005) Zimmer, Inc. 4 sheets.
Birnbaum, Klaus, M.D., "Computer-Assisted Orthopedic Surgery With Individual Templates and Comparison to Conventional Method," Spine vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knieendoprothese," Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazen, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.
International Preliminary Report on Patentability mailed Mar. 31, 2011 for PCT/US2009/056670 claiming benefit of U.S. Appl. No. 12/211,407, filed Sep. 16, 2008.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.
International Search Report and Written Opinion for PCT/US2009/056670 mailed Mar. 2, 2010 claiming benefit of U.S. Appl. No. 12/211,407, filed Sep. 16, 2008.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 10, 2010 for PCT/US2010/038177 claiming benefit of U.S. Appl. No. 12/483,807, filed Jun. 12, 2009.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Oct. 5, 2010 for PCT/US2010/038845 claiming benefit of U.S. Appl. No. 12/486,992, filed Jun. 18, 2009.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-158. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

(56) References Cited

OTHER PUBLICATIONS

Portheine, F., et al., Entwicklung eines klinischen Demonstrators für die computerunterstützte Orthopädische Chirurgie mit CT-Bildbasierten Individualschablonen, Bildverarbeitung für die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&Issue . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Biomet "Oxford® Partial Knee" brochure, 8 pages. (Feb. 2011).

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

"Comprehensive® Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

Friedman, R.J. et al., "The Use of Computerized Tomography in the Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478, filed Aug. 29, 2011.

International Search Report and Written Opinion mailed Feb. 6, 2013 for PCT/US2012/060842, which claims benefit of U.S. Appl. No. 13/653,868, filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability and Written Opinion mailed Jan. 3, 2014 for PCT/US2012/042081 claiming benefit of U.S. Appl. No. 13/493,509, filed Jun. 11, 2012.

International Preliminary Report on Patentability and Written Opinion mailed Nov. 28, 2013 for PCT/US2012/038351 claiming benefit of U.S. Appl. No. 13/111,007, filed May 19, 2011.

International Preliminary Report on Patentability mailed Sep. 6, 2013 for PCT/US2012/026356 claiming benefit of U.S. Appl. No. 13/041,883, filed Mar. 7, 2011.

International Search Report and Written Opinion mailed Oct. 14, 2013 for PCT/US2013/057097 claiming benefit of U.S. Appl. No. 13/597,478, filed Aug. 29, 2012.

\* cited by examiner

ALIGNMENT GUIDES WITH PATIENT-SPECIFIC ANCHORING ELEMENTS

CROSS-REFERENCE TO RELATED APPLICATIONS

This application claims the benefit of U.S. Provisional Application No. 61/446,660, filed on Feb. 25, 2011.

This application is a continuation-in-part of U.S. application Ser. No. 12/978,069 filed Dec. 23, 2010, which is a continuation-in-part of U.S. application Ser. No. 12/973,214, filed Dec. 20, 2010, which is a continuation-in-part of U.S. application Ser. No. 12/955,361 filed Nov. 29, 2010, which is a continuation-in-part of U.S. application Ser. Nos. 12/938,905 and 12/938,913, both filed Nov. 3, 2010, each of which is a continuation-in-part of U.S. application Ser. No. 12/893,306, filed Sep. 29, 2010, which is a continuation-in-part of U.S. application Ser. No. 12/888,005, filed Sep. 22, 2010, which is a continuation-in-part of U.S. application Ser. No. 12/714,023, filed Feb. 26, 2010, which is: a continuation-in-part of U.S. application Ser. No. 12/571,969, filed Oct. 1, 2009, which is a continuation-in-part of U.S. application Ser. No. 12/486,992, filed Jun. 18, 2009, and is a continuation-in-part of U.S. application Ser. No. 12/389,901, filed Feb. 20, 2009, which is a continuation-in-part of U.S. application Ser. No. 12/211,407, filed Sep. 16, 2008, which is a continuation-in-part of U.S. application Ser. No. 12/039,849, filed Feb. 29, 2008, which: (1) claims the benefit of U.S. Provisional Application No. 60/953,620, filed on Aug. 2, 2007, U.S. Provisional Application No. 60/947,813, filed on Jul. 3, 2007, U.S. Provisional Application No. 60/911,297, filed on Apr. 12, 2007, and U.S. Provisional Application No. 60/892,349, filed on Mar. 1, 2007; (2) is a continuation-in-part U.S. application Ser. No. 11/756,057, filed on May 31, 2007, which claims the benefit of U.S. Provisional Application No. 60/812,694, filed on Jun. 9, 2006; (3) is a continuation-in-part of U.S. application Ser. No. 11/971,390, filed on Jan. 9, 2008, which is a continuation-in-part of U.S. application Ser. No. 11/363,548, filed on Feb. 27, 2006; and (4) is a continuation-in-part of U.S. application Ser. No. 12/025,414, filed on Feb. 4, 2008, which claims the benefit of U.S. Provisional Application No. 60/953,637, filed on Aug. 2, 2007.

This application is continuation-in-part of U.S. application Ser. No. 12/872,663, filed on Aug. 31, 2010, which claims the benefit of U.S. Provisional Application No. 61/310,752 filed on Mar. 5, 2010.

This application is a continuation-in-part of U.S. application Ser. No. 12/483,807, filed on Jun. 12, 2009, which is a continuation-in-part of U.S. application Ser. No. 12/371,096, filed on Feb. 13, 2009, which is a continuation-in-part of U.S. application Ser. No. 12/103,824, filed on Apr. 16, 2008, which claims the benefit of U.S. Provisional Application No. 60/912,178, filed on Apr. 17, 2007.

This application is also a continuation-in-part of U.S. application Ser. No. 12/103,834, filed on Apr. 16, 2008, which claims the benefit of U.S. Provisional Application No. 60/912,178, filed on Apr. 17, 2007.

The disclosures of the above applications are incorporated herein by reference.

INTRODUCTION

The present teachings provide various alignment guides with patient-specific anchoring elements for joint arthroplasty.

SUMMARY

The present teachings provide an orthopedic device for joint arthroplasty. The orthopedic device includes an alignment guide and a number of patient-specific anchoring elements. The alignment guide can be mounted on a bone of a patient during joint arthroplasty. The patient-specific anchoring elements extend from an inner surface of the alignment guide and have a patient-specific length relative to an outer bone surface of the bone of the patient.

In some embodiments, a patient-specific anchoring element includes including a first portion designed to penetrate through articular cartilage and a second portion designed to penetrate through an outer surface of the bone underlying the articular cartilage for anchoring the alignment guide in the bone. In some embodiments, anchoring element includes a shoulder between the first and second portions. The shoulder is designed to abut on the outer surface of the bone. In some embodiments, the first portion is patient-specific and has a length equal to the thickness of the specific patient's cartilage at the corresponding location of the bone.

The present teachings also provide a method for preparing a bone of a joint during joint arthroplasty. In some embodiments, the method includes mounting an alignment guide on a bone of a joint of a patient along an alignment direction, and anchoring the alignment guide into a cartilage of the bone using a plurality of patient-specific anchoring elements extending from an inner surface of alignment guide. Each anchoring element has a patient-specific length extending between the inner surface and an end point of the corresponding anchoring element.

In some embodiments, the method includes mounting an alignment guide on an outer cartilage surface of an articular cartilage of an underlying bone of the patient. The alignment guide is anchoring on the patient's anatomy using a plurality of patient specific anchoring elements extending from a cartilage-engaging surface of alignment guide. The method further includes penetrating the cartilage with cartilage-engaging portions of the anchoring elements, and penetrating an outer bone surface of the underlying bone with bone-engaging portions of the anchoring elements. The lengths of the cartilage-engaging portions of the anchoring elements can be determined from the cartilage thickness at corresponding locations of the bone of the patient. The cartilage thickness at each anchoring location can be determined from a three-dimensional computer image of the bone and articular cartilage reconstructed from medical scans of the patient during a preoperative plan for the patient.

The alignment guides can be designed for the articular surfaces of a joint, such as, for example, a knee, hip or shoulder joint. In some embodiments a plurality of anchoring elements uniformly or randomly distributed over the anatomy-engaging surface of the alignment guide are used. In some embodiments, a small number of anchoring elements are used, such as, for example, three non-collinear anchoring elements.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS AND EMBODIMENTS

Figure 1:
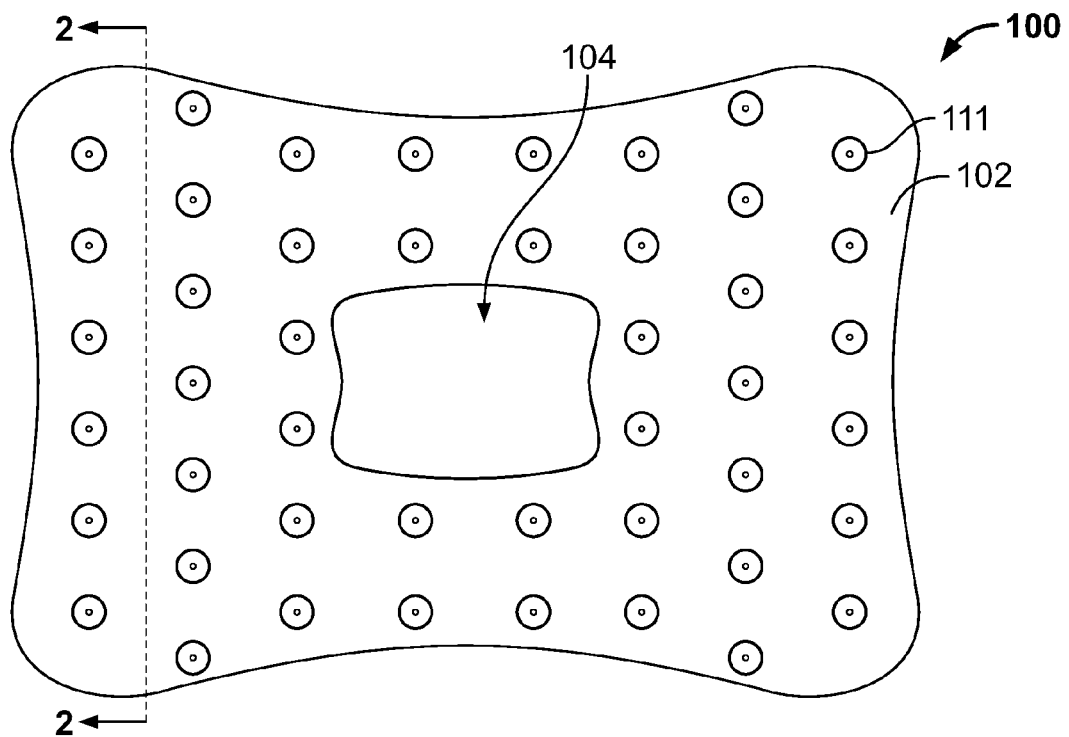
FIG. 1 is a plan view of a patient-specific alignment guide with anchoring elements according to the present teachings.

The following description is merely exemplary in nature and is in no way intended to limit the present teachings, applications, or uses.

The present teachings generally provide various patient-specific alignment and resection guides and other associated instruments for use in orthopedic surgery, such as, for example, in joint replacement or revision surgery. The patient-specific guides can be used either with conventional or patient-specific implant components and can be prepared with computer-assisted image methods. Computer modeling for obtaining three-dimensional (3-D) images of the patient's anatomy using MRI or CT scans of the patient's anatomy, modeling of patient-specific prosthesis components and the patient-specific guides and templates can be configured and designed using various commercial CAD programs and/or software, such as, for example, software by Materialise USA, Ann Arbor, Mich.

Patient-specific alignment guides and implants are generally configured to match the anatomy of a specific patient. The patient-specific alignment guides are generally formed using computer modeling based on the patient's 3-D anatomic image and have an engagement surface that is made to conformingly contact and match a three-dimensional image of the patient's bone surface (with or without cartilage or other soft tissue) in only one position, by the computer methods discussed above. The patient-specific alignment guides are designed and prepared preoperatively using anatomic landmarks, such as osteophytes, for example, and can be mounted intra-operatively without any registration or other guidance based on their unique patient-specific surface guided by the patient's anatomic landmarks.

The patient-specific alignment guides can include custom-made guiding formations, such as, for example, guiding bores or cannulated guiding posts or cannulated guiding extensions or receptacles that can be used for supporting or guiding other non-custom instruments, such as drill guides, reamers, cutters, cutting guides and cutting blocks or for inserting pins or other fasteners according to a surgeon-approved pre-operative plan for performing various resections as indicated for an arthroplasty, joint replacement, resurfacing or other procedure for the specific patient.

The patient-specific guides can also include resection or cutting formations, such as cutting slots or cutting edges or planes used for guiding a cutting blade to perform bone resections directly through the patient-specific cutting guide. The patient-specific guides can be used in minimally invasive surgery. Various alignment/resection guides and preoperative planning procedures are disclosed in commonly assigned and co-pending U.S. patent application Ser. No. 11/756,057, filed on May 31, 2007; U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; and U.S. patent application Ser. No. 12/025,414, filed Feb. 4, 2008. The disclosures of the above applications are incorporated herein by reference.

As disclosed, for example, in the above-referenced U.S. patent application Ser. No. 11/756,057, filed on May 31, 2007, in the preoperative planning stage for a joint replacement or revision procedure, an MRI scan or a series of CT scans of the relevant anatomy of the patient, such as, for example, the entire leg of the joint to be reconstructed, can be performed at a medical facility or doctor's office. The scan data obtained can be sent to a manufacturer. The scan data can be used to construct a three-dimensional image of the joint and provide an initial implant fitting and alignment in a computer file form or other computer representation. The initial implant fitting and alignment can be obtained using an alignment method, such as alignment protocols used by individual surgeons.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer/digital file form associated with interactive software, can be sent to the surgeon, or other medical practitioner, for review. The surgeon can incrementally manipulate the position of images of various implant components in an interactive image of the joint. Additionally, the surgeon can select or modify resection planes, types of implants and orientations of implant insertion. After the surgeon modifies and/or approves the surgical plan, the surgeon can send the final, approved plan to the manufacturer.

After the surgical plan is approved by the surgeon, patient-specific alignment/resection guides can be designed by configuring and using a CAD program or other imaging software, such as the software provided by Materialise, for example, according to the surgical plan. Computer instructions of tool paths for machining the patient-specific alignment guides can be generated and stored in a tool path data file. The tool path can be provided as input to a CNC mill or other automated machining system, and the alignment guides can be machined from polymer, ceramic, metal or other suitable material. The guides can also be manufactured by various other methods, stereolithography, laser deposition, printing, and rapid prototyping methods. The alignment guides are sterilized and shipped to the surgeon or medical facility, for use during the surgical procedure. Various patient-specific knee alignment guides and associated methods are disclosed in the commonly assigned U.S. application Ser. No. 11/756,057, filed on May 31, 2007 (published as 2007/0288030 on Dec. 13, 2007), which is incorporated herein by reference.

A patient-specific alignment guide can be used to drill holes through corresponding bone of the joint surface and to guide alignment pins through the holes. The alignment guide is then removed leaving the alignment pins for supporting and cutting instruments to make various resections in the bone in preparation for receiving a joint implant.

The various patient-specific alignment guides can be made of any biocompatible material, including, polymer, ceramic, metal or combinations thereof. The patient-specific alignment guides can be disposable and can be combined or used with other reusable non patient-specific cutting and guiding components.

Figure 2:
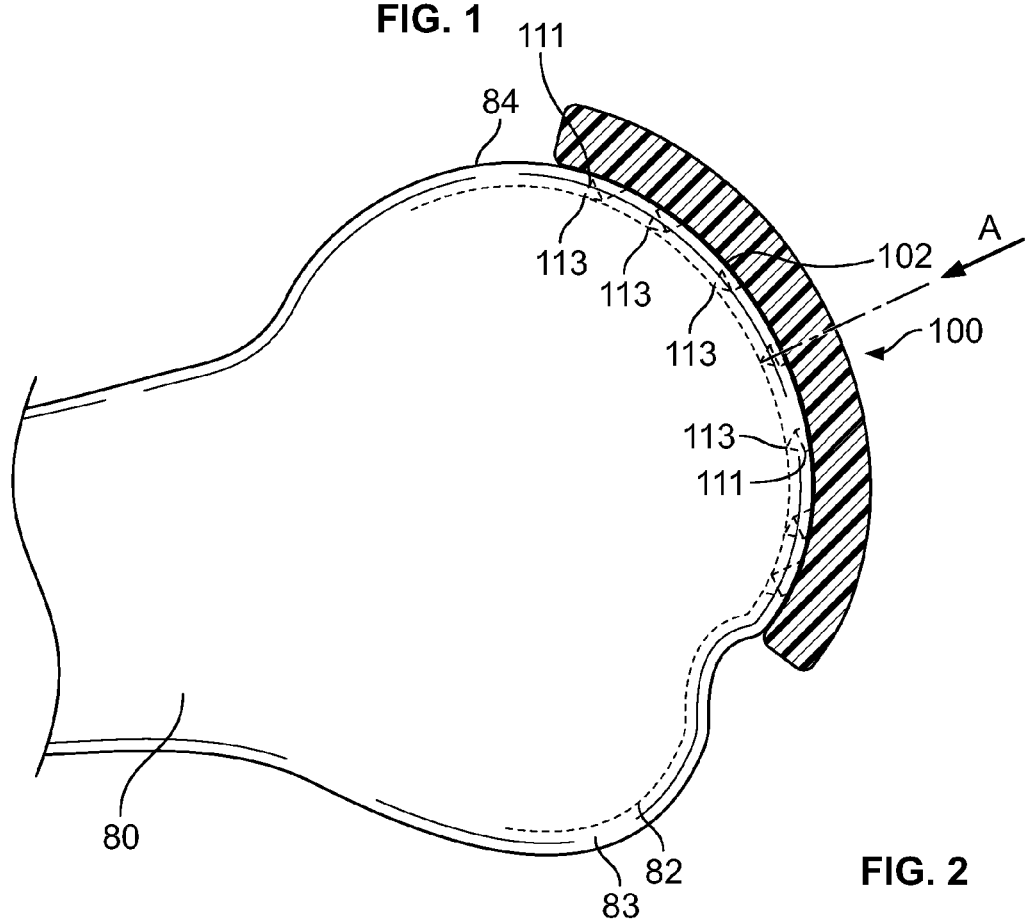
FIG. 2 is an environmental sectional view of a patient-specific alignment guide with anchoring elements according to the present teachings.

Referring to FIGS. 1 and 2, an exemplary alignment guide 100 is generally illustrated according to the present teachings. The alignment guide 100 has a three-dimensional, curved inner surface 102. In some embodiments, the inner surface 102 nestingly matches and is complementary to a corresponding surface of a patient including various anatomic landmarks, such that the alignment guide 100 can be positioned and nested only in one position relative to the anatomy of the specific patient along an alignment orientation A. The patient's anatomy can be, for example, a bone 80 related to a joint of the patient and including a layer of articular cartilage 83 over an outer bone surface 82. The articular cartilage 83 can extend between the outer bone surface 82 and an outer cartilage surface 84. In this embodiment, the inner surface 102 of the patient-specific guide 100 is designed to match and mate with the outer cartilage surface 84. The alignment guide 100 is designed to be light-weight and can include various cut-outs or windows, such as 104. The alignment guide 100 can include a plurality of patient-specific anchoring elements 111 with end points 113. The anchoring elements 111 can be, for example, spikes, or teeth or pins extending from the anatomy-engaging surface 102 and sized and configured to penetrate the cartilage up to the outer bone surface 82. The anchoring elements 111 can be engage the cartilage 83 at several points for providing three-dimensional anchoring stability. Multiple anchoring elements 111, such as, for example, five or more, can be positioned uniformly or randomly relative to the inner surface 102. Alternatively, a few anchoring elements 111, such as, for example about three to five, can be included at selected or pre-determined and relative positions.

In some embodiments, the anchoring elements 111 can be configured to be parallel to an alignment/mounting direction A for mounting and removing the guide 100, as shown in FIG. 2. Using parallel anchoring elements 111 can avoid tearing the cartilage and thereby reducing the anchoring stability of the alignment guide 100. The alignment/mounting direction can be determined during the preoperative plan for the patient. In some embodiments, the three-dimensional shape of the outer bone surface 82 (and, optionally, the outer cartilage surface 84) can be represented in three-dimensional computer models generated from the medical scans of the patient and used to design the variable and patient-specific height (or length) of each anchoring element 111 such that a geometric envelope of the end points 113 traces a surface complementary and mating with the outer bone surface 82. Accordingly, only the outer bone surface 82 needs to be imaged using standard bone imaging methods, such as CT and two-dimensional X-rays, for example. Therefore, for these embodiments, is not necessary to use methods, such as MRI, that can image the cartilage or other soft tissue. In some embodiments, the length of the anchoring elements is patient-specific. In some embodiments, the length of the anchoring elements 111 can be greater that the corresponding thickness of the cartilage 83, such that the inner surface 102 of the alignment guide 100 does not contact the cartilage.

In some embodiments, each anchoring element 111 can have a length extending from the end point 113 to the inner surface 102 and approximating the thickness of the articular cartilage 83 of the particular bone 80 of the patient at each specific location of the anchoring element 111. The thickness of the cartilage 83 can generally vary with the topography of the joint, i.e., the cartilage distribution is non-uniform over a bone surface for a single patient. There may also be additional gender-, age-, weight- and disease-related cartilage variations. The cartilage of a specific patient can also have various defects or other idiosyncratic features. A detailed cartilage topography of a specific patient can be determined during the pre-operative plan from medical scans/images that can depict bone and soft tissue surfaces, such as, for example, MRI images, CT images or other imaging methods capable of showing bone and/or soft tissue.

In some embodiments, a uniform and constant height can be selected for all the anchoring elements, equal, for example, to the mean or the median or maximum or other value based on the thickness variation of the cartilage of a particular joint surface of the patient. When the maximum thickness of the cartilage is used as the height of all the anchoring elements 111, the inner surface 102 of the patient-specific guide 100 may not contact points of the outer cartilage surface 84 where the cartilage 83 is thinner than the maximum, i.e., there may be some areas of non-contact forming gaps between the cartilage 83 and the anatomy-engaging surface 102. Depending on the location of the cartilage 83, the thickness of the cartilage 103 can vary from 0 to 6-7 mm, with higher thickness generally corresponding to the knee patella of healthy young males. In some embodiments, the inner surface 102 of the guide 100 does not engage the cartilage 83 at all.

Figure 3:
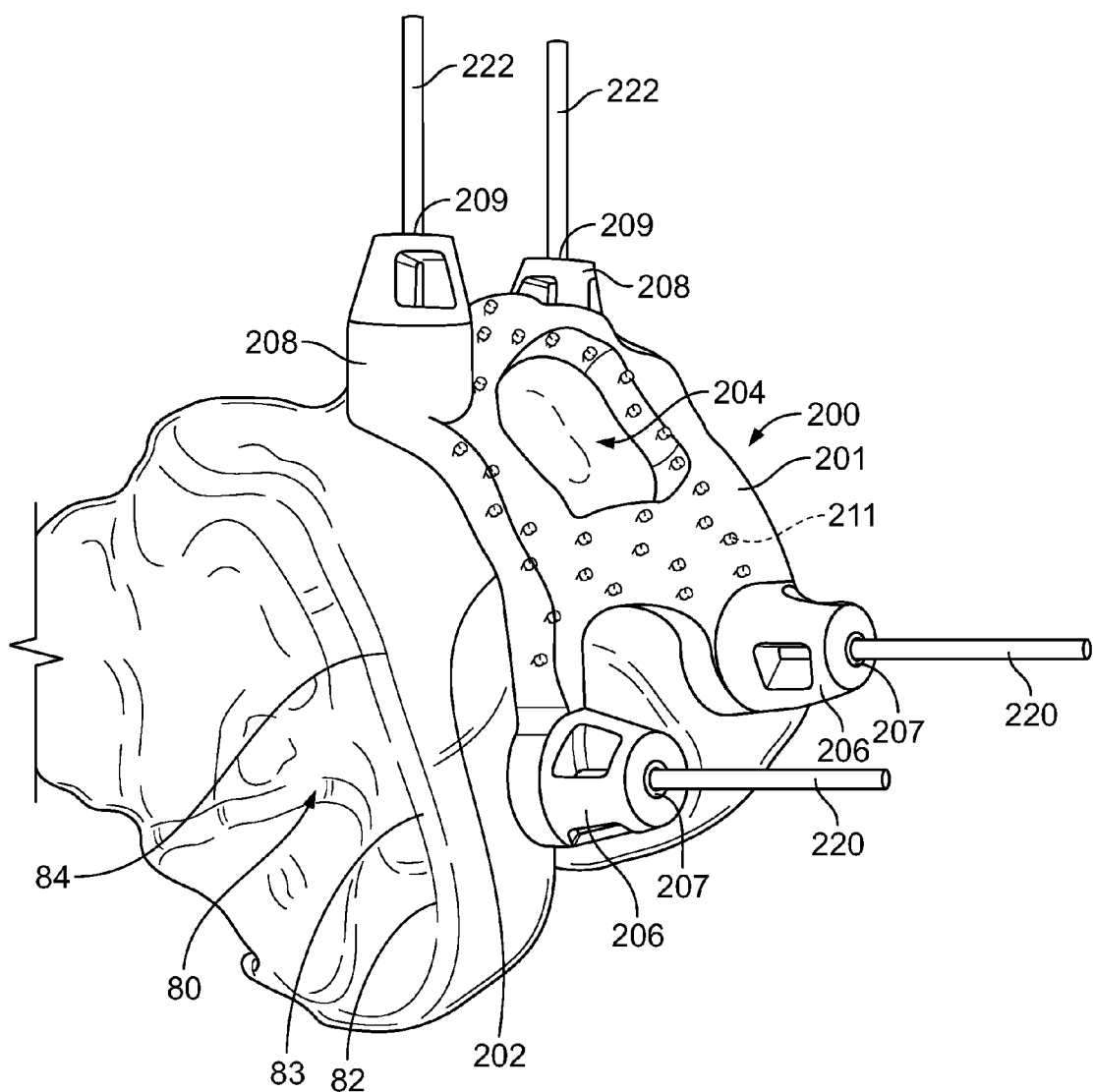
FIG. 3 is an environmental perspective view of a patient-specific femoral alignment guide with anchoring elements according to the present teachings.

Referring to FIG. 3, an exemplary femoral alignment guide 200 according to the present teachings is configured for use with the patient's distal femoral bone 80 (an example of the bone 80 of FIG. 2). The femoral alignment guide 200 can have a light-weight body 201 with a three-dimensional inner surface 202. In some embodiments, the inner surface 202 may be a patient-specific engagement surface that is complementary and made to closely conform and mate with a portion of the anterior-distal articulating or outer cartilage surface 84 of the patient's femur 80 based on the pre-operative plan, as described above. The femoral alignment guide 200 can include a window/opening 204 and first and second distal guiding formations 206 defining guiding bores 207 for guiding corresponding distal alignment pins 220. The femoral alignment guide 200 can also include first and second anterior guiding formations 208 defining guiding bores 209 for drilling holes through the distal femur 80 and guiding corresponding anterior alignment pins 222. Additionally, the femoral alignment guide 200 can include a plurality of anchoring elements 211 that are similar to the anchoring elements 111 described above in reference to FIG. 2. The anchoring elements 211 are also designed to penetrate the articular cartilage 83 for preventing small rotational and/or translational displacements of the femoral alignment guide 200 during use. The anchoring elements 211 can be distributed randomly or uniformly to penetrate the entire outer cartilage surface 84 which the patient-specific femoral guide 200 engages. Alternatively, a few discrete anchoring elements 211 can be used instead, including at least three elements. The anchoring elements 211 can be parallel defining an alignment/mounting direction for inserting and removing the femoral alignment guide 200, as discussed above in connection with FIG. 2, and can engage the cartilage at points arranged in a three-dimensional pattern for providing anchoring stability. The length of the anchoring elements 211 can be variable and patient-specific such that a geometric envelope of their end points traces a surface complementary and mating with the outer bone surface 82.

Figure 4:
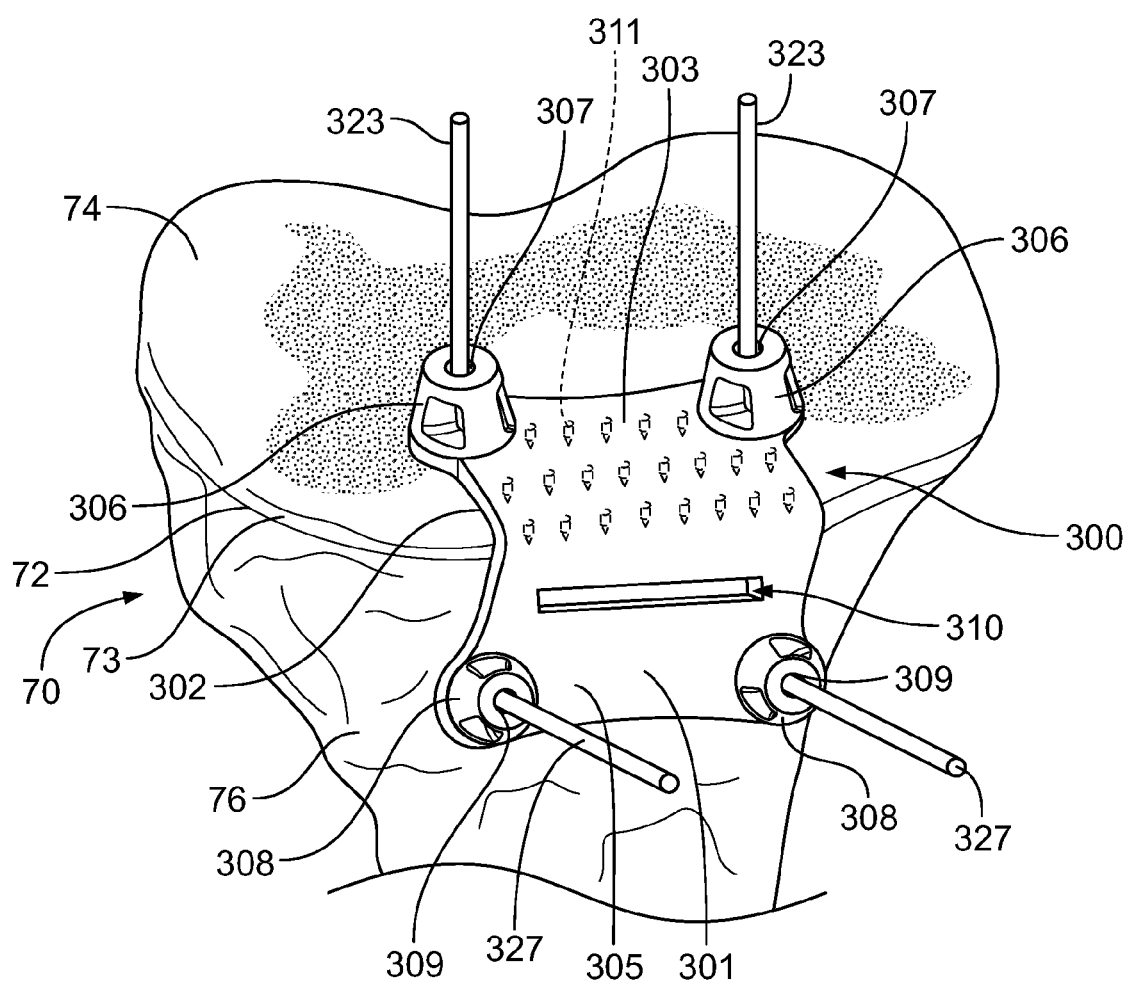
FIG. 4 is an environmental perspective view of a patient-specific tibial guide with anchoring elements according to the present teachings.

Referring to FIG. 4, a representative tibial alignment/resection guide 300 is illustrated according to the present teachings. The tibial alignment guide 300 can include a body 301 having a proximal portion 303, an anterior portion 305 and a three-dimensional inner surface 302. In some embodiments, the inner surface can be a patient-specific surface that is complementary and made to closely conform and mate with a portion of an anterior surface 76 and a portion of a proximal surface or outer cartilage surface 74 of the patient's tibia 70 in only one position based on the pre-operative plan. The tibial alignment guide 300 can include first and second proximal guiding formations 306 defining guiding bores 307 for corresponding proximal alignment pins or other fasteners 323. The tibial alignment/resection guide 300 can also include first and second anterior guiding formations 308 defining guiding bores 309 for corresponding anterior alignment pins or other fasteners 327. As discussed above in connection with alignment guides in general and the femoral alignment guide 200 in particular, the tibial alignment guide 300 can be used to drill reference holes for the corresponding proximal and anterior alignment pins 323, 327, which can then be re-inserted as needed for each resection and corresponding resection block after the tibial alignment/resection guide 300 is removed. The tibial alignment/resection guide 300 can optionally include a resection guiding slot 310 for guiding a tibial resection according to the pre-operative plan for the patient. Additionally, the tibial alignment guide 300 can include a plurality of anchoring elements 311 that are similar to the anchoring elements 111 described above in reference to FIG. 2. The anchoring elements 311 are designed to penetrate the tibial cartilage 73 for preventing small rotational and/or translational displacements of the tibial alignment guide 300 during use. The anchoring elements 311 can be distributed randomly or uniformly to penetrate the tibial cartilage 73 between the bone surface 72 and the outer cartilage surface 74 of the proximal tibia over the area that the proximal portion 303 of the patient-specific tibial alignment guide 300 engages. Alternatively, a few discrete anchoring elements 311 can be used instead, including at least three elements in a three-dimensional arrangement. Generally, the anchoring elements 311 can be parallel to an alignment/mounting direction (see FIG. 2) and engage the cartilage at points arranged in a three-dimensional pattern for stability. The length of the anchoring elements 311 can be variable and patient-specific such that a geometric envelope of their end points traces a surface complementary and mating with the outer bone surface 72, as discussed above.

Figure 5:
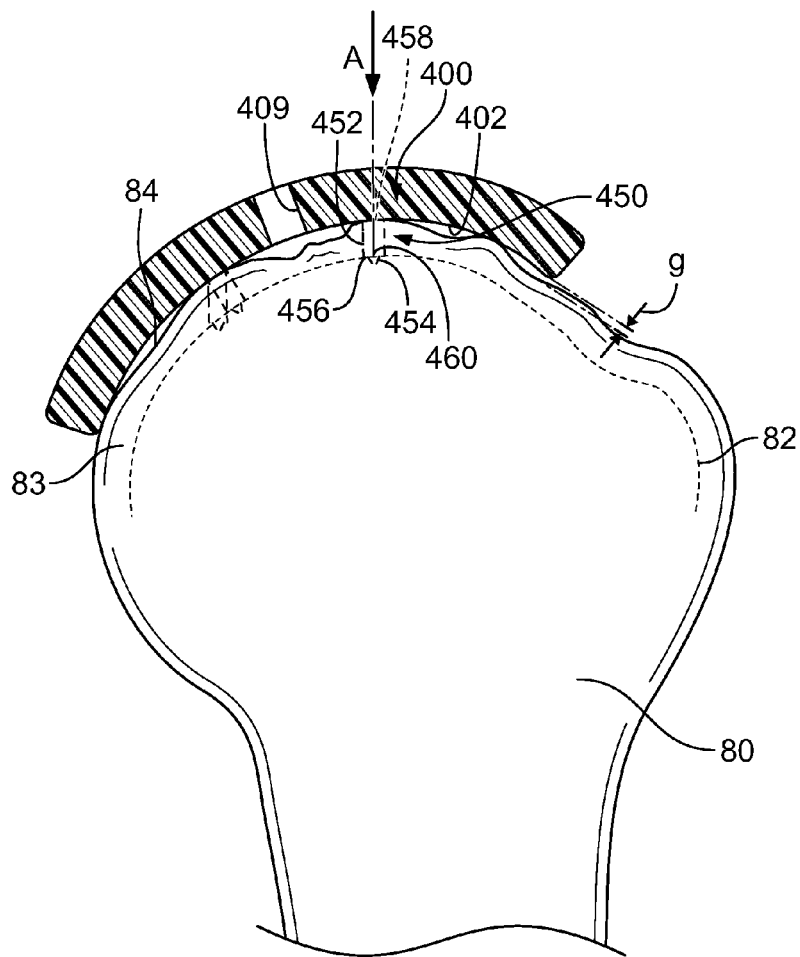
FIG. 5 is an environmental sectional view of a patient-specific alignment guide with anchoring elements according to the present teachings.
Figure 5A:
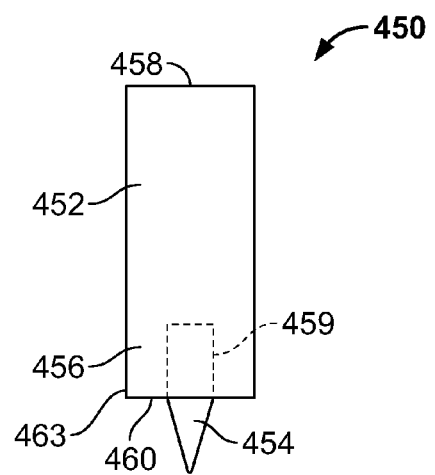
FIG. 5A is a detail of an anchoring element of FIG. 5.
Figure 6:
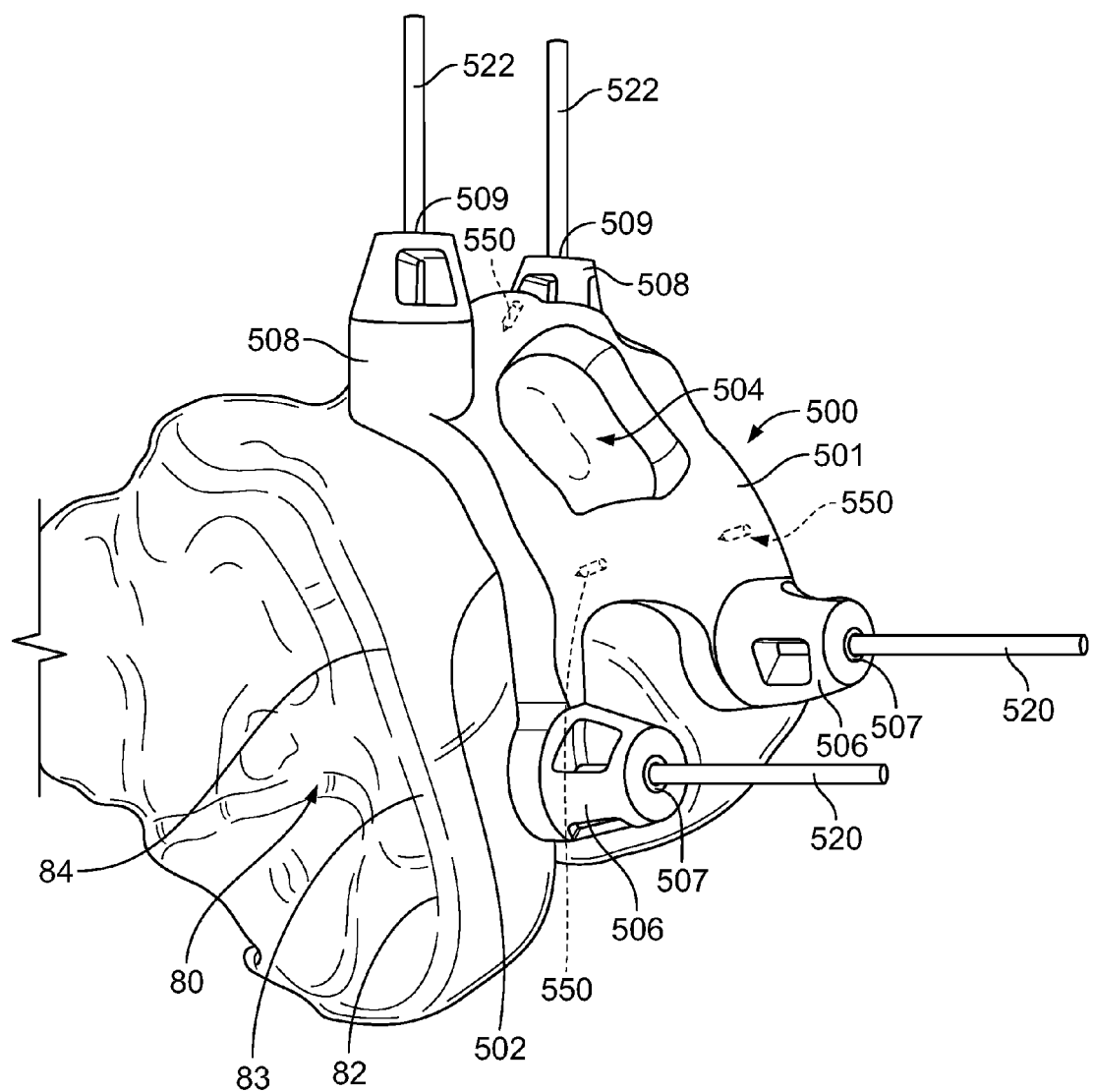
FIG. 6 is an environmental perspective view of a patient-specific femoral alignment guide with anchoring elements according to the present teachings.
Figure 7:
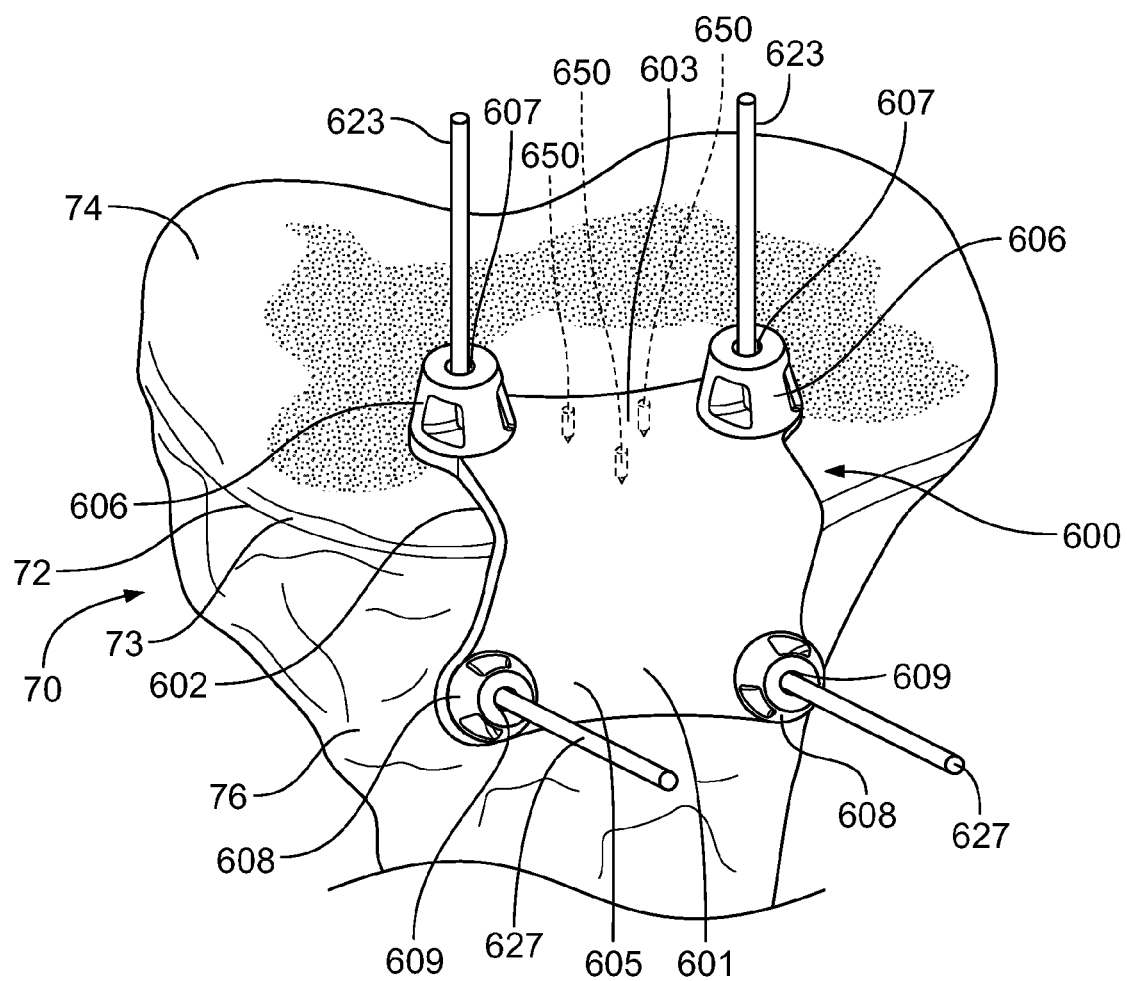
FIG. 7 is an environmental perspective view of a patient-specific tibial guide with anchoring elements according to the present teachings.

Referring to FIGS. 5 and 5A, a detail of an alignment guide 400 with patient-specific anchoring elements 450 is illustrated according to the present teachings. FIG. 6 illustrates a femoral alignment guide 500 similar to the femoral alignment guide 200, but with patient-specific anchoring elements 550 similar to the patient-specific anchoring elements 450 of FIG. 5. Similar elements between alignment guides 200 and 500 are referenced with numerals having the same second and third digits. FIG. 7 illustrates a tibial alignment guide 600 similar to the tibial alignment guide 300, but with patient-specific anchoring elements 650 similar to the patient-specific anchoring elements 450 of FIG. 5. Similar elements between alignment guides 300 and 600 are referenced with numerals having the same second and third digits. The patient-specific anchoring elements 450, 550 and 650 are similar and are described in reference to FIG. 5, which illustrates generically a portion of a patient-specific alignment guide 400. At least three anchoring elements 450 in a three dimensional pattern can be used for providing anchoring stability in three dimensions. In some embodiments, the alignment guides 400, 500 and 600 can also be patient-specific with three-dimensional cartilage engaging surfaces that can nestingly mate to and be mounted on the outer surface of the articular cartilage of the patient in only one position.

The patient-specific anchoring elements 450 can be designed using a three-dimensional computer image of the patient's anatomy including the articular cartilage surface and the underlying bone during a preoperative plan for the patient. The three-dimensional image can be constructed based on medical scans of the patient, such as MRI, CT, ultrasound or other scans equipped or modified to image soft tissue, such as articular cartilage and using commercially available CAD/CAD imaging software.

Referring to FIGS. 5 and 5A, the patient-specific anchoring elements 450 are configured for penetrating the articular cartilage 83 and anchoring into the underlying bone 80 through the outer bone surface 82. Each anchoring element 450 can include a cartilage-anchoring portion 452 and a bone-anchoring portion 454. The cartilage-anchoring portion 452 can be in the form of an elongated element having a first end 458 attached to an anatomy-engaging surface 402 of the alignment guide 400 and an opposite second end 456 in the form of a patient-specific surface 460 designed for abutting and closely mating with the outer bone surface 82. The geometric envelope of the patient-specific surfaces 460 of all the anchoring elements 450 can be designed during the pre-operative plan to be patient-specific relative to the outer bone surface 82, such that the surface 460 to be complementary and closely mate and conform to the outer bone surface 82. Accordingly, the length of each cartilage-anchoring portion 452 from the first end 458 to the second end 456 is patient-specific and can be selected to be equal to the thickness of the patient's cartilage 83 at the corresponding location for each anchoring element 450. The bone-anchoring portion 454 can be in the form of a spike or pin extending from the second end 456 of the cartilage-anchoring portion 452 for penetrating the outer bone surface 82 and lodging into the bone 80.

With continued reference to FIGS. 5 and 5A, the patient-specific surface 460 forms a shoulder or step 463 between the second end 456 of the cartilage-anchoring portion 452 and the bone-anchoring portion 454. The cartilage-anchoring portion 452 penetrates the cartilage 83 and can be seated in a pocket formed in the cartilage 83 when the alignment guide 400 is pressed against the bone 80 until the bone-anchoring portion 454 penetrates the bone 80 and the patient-specific surface 460 nestingly mates and seats on the outer bone surface 82 under the cartilage. The bone anchoring portion 454 can be made of a material of sufficient strength and/.or rigidity to penetrate the bone 80. In some embodiments, the bone anchoring portion 454 and the cartilage-anchoring portion 452 can be made of different materials. In some embodiments, the bone-anchoring portion 454 can be made separately from the cartilage-anchoring portion 452 and have a portion 459 inserted permanently or removably into the cartilage-anchoring portion 452. In other embodiments, the bone anchoring portion 454 and the cartilage-anchoring portion 452 can be made as one integral or monolithic piece. In some embodiments, the anchoring elements can be parallel to an alignment orientation A. In some embodiments, the anchoring elements can be perpendicular to bone surface 82.

With continued reference to FIGS. 5 and 5A, the cartilage-engaging surface 402 can be designed during the pre-operative plan of the patient as a three-dimensional patient-specific surface that complementarily and nestingly mates with the outer cartilage surface 84 in only one position. In some embodiments, conformance to small variations, such as minute defects, in the outer cartilage surface 84 may be relaxed, although the alignment guide 400 can still be mounted on the outer cartilage surface in only one position and is still patient-specific. In this respect, a small gap "g" may be formed between the outer cartilage surface 84 and the anatomy-engaging surface 402 of the alignment guide 400 in certain locations depending on the profile and condition of the cartilage 83. The cartilage-anchoring portion 452 of each anchoring element 450 has a patient specific length and a patient-specific bone-abutting surface 460. The cartilage-anchoring portion 452 can generally have a diameter or major cross-sectional dimension of about 2-5 mm, while the major cross-sectional dimension of the bone-anchoring portion 454 can be about 1-2 mm. The gap g can also be of the order of 1-2 mm.

As discussed above, the patient-specific anchoring elements 111, 211, 311, 450, 550, 650 can be integrated with various patient-specific guides designed to engage a cartilage bearing articulating surface of a joint, such as the distal femur and the proximal tibia for a knee joint. The patient-specific anchoring elements can also be used, for example, with guides designed to engage the articular surfaces of the hip joint or shoulder joint.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An orthopedic device for joint arthroplasty comprising:
   an alignment guide mountable on a bone of a patient during joint arthroplasty; and
   a plurality of patient-specific anchoring elements extending from an inner surface of the alignment guide and having a patient-specific length relative to an outer bone surface of the bone of the patient, the patient-specific length is a custom length based on a multi-dimensional image of the patient's bone surface and soft tissue covering the bone surface;
   wherein the inner surface is a three-dimensional patient-specific surface including a customized shape based on a multi-dimensional image of an outer cartilage surface of the bone of the patient and configured to nestingly mate to and be mounted on the outer cartilage surface of the bone of the patient in only one position.

2. The orthopedic device of claim 1, wherein each patient-specific anchoring element includes a corresponding end point, and the plurality of the end points define a geometric envelope surface that traces a surface complementary and mating with the outer bone surface.

3. The orthopedic device of claim 1, wherein the patient-specific anchoring elements are parallel to an alignment direction.

4. The orthopedic device of claim 1, wherein the soft tissue includes cartilage and the anchoring elements are configured to penetrate through an outer cartilage surface of the bone and penetrate through the outer bone surface of the bone for anchoring the alignment guide on the bone of the patient.

5. The orthopedic device of claim 4, wherein each anchoring element includes a patient-specific cartilage-anchoring portion and a bone-anchoring portion, the cartilage-anchoring portion having first and second ends, the first end extending from the inner surface of the alignment guide, the bone-anchoring portion extending from a portion of the second end of the cartilage-anchoring portion.

6. The orthopedic device of claim 5, wherein a length extending between the first and second ends of the cartilage-anchoring portion is patient-specific and customized for the patient according to a multi-dimensional image of the patient's cartilage covering the bone surface to equal a thickness of the cartilage at the corresponding location on the patient's bone.

7. The orthopedic device of claim 5, wherein the second end of the cartilage-anchoring portion has a patient-specific surface designed to contact and mate with the outer surface of the bone at the corresponding location on the bone.

8. The orthopedic device of claim 5, wherein each anchoring element includes a shoulder between the bone-anchoring portion and the cartilage-anchoring portion, the shoulder configured to abut the outer surface of the bone.

9. The orthopedic device of claim 5, wherein the cartilage-anchoring portion and the bone-anchoring portion are made of different materials.

10. The orthopedic device of claim 5, wherein the bone-anchoring portion includes an end point for penetrating bone.

11. The orthopedic device of claim 1, wherein the alignment guide is a femoral guide configured to be mounted on a distal femoral bone.

12. The orthopedic device of claim 1, wherein the alignment guide is a tibial guide configured to be mounted on a proximal tibial bone.

13. The orthopedic device of claim 1, wherein the patient-specific anchoring elements are randomly distributed over the alignment guide.

14. The orthopedic device of claim 1, wherein the patient-specific anchoring elements are uniformly distributed over the alignment guide.

15. The orthopedic device of claim 1, wherein the plurality of patient-specific anchoring elements includes at least three anchoring elements.

16. The orthopedic device of claim 1, wherein the plurality of patient-specific anchoring elements includes five or more anchoring elements.

17. The orthopedic device of claim 1, wherein the alignment guide includes guiding bores for guiding alignment pins.

18. The orthopedic device of claim 1, wherein the alignment guide is a tibial alignment guide including a first portion engageable to a portion of a proximal surface of a tibial bone of a patient and a second portion engageable to a portion of an anterior surface of the tibial bone.

19. The orthopedic device of claim 18, wherein the anchoring elements extend only from the first portion of the alignment guide for anchoring through cartilage of the proximal surface of the tibial bone.

20. The orthopedic device of claim 1, wherein each one of the patient-specific anchoring elements include a first portion and a second portion extending from the first portion, the first portion configured to extend only to the outer bone surface and the second portion configured to extend into the outer bone surface.

21. An orthopedic device for joint arthroplasty comprising:
an alignment guide including an inner surface configured to be mounted on an outer articular cartilage surface of an underlying bone of the patient; and
a first anchoring element extending from the inner surface, the first anchoring element including a first portion designed to penetrate through articular cartilage and a second portion designed to penetrate through an outer surface of the bone underlying the articular cartilage for anchoring the alignment guide on the bone, the first anchoring element including a shoulder between the first and second portions, the shoulder designed to abut on the outer surface of the bone;
wherein the inner surface is a three-dimensional patient-specific surface including a customized shape based on a multi-dimensional image of an outer cartilage surface of the bone of the patient and configured to nestingly mate to and be mounted on the outer cartilage surface of the bone of the patient in only one position.

22. The orthopedic device of claim 21, wherein the first portion is patient-specific and has a length equal to a thickness of the specific patient's cartilage at the corresponding location of the bone, the length is a custom patient-specific length corresponding to a multi-dimensional image of the patient's cartilage.

23. The orthopedic device of claim 22, further comprising a second and third anchoring element, each anchoring element including a shoulder between respective first and second portions, the shoulders designed during a pre-operative plan of the patient to form a geometric envelope surface complementary to the outer surface of the bone for abutting on the outer surface of the bone.

24. An orthopedic device for joint arthroplasty of a patient comprising:
an alignment guide including an inner anatomy-engaging surface configured to be mounted on an outer articular cartilage surface of an underlying bone of the patient;
a plurality of patient-specific anchoring elements extending from the inner anatomy-engaging surface, each one of the plurality of patient-specific anchoring elements including:
a cartilage anchoring portion including a first end coupled to the inner anatomy-engaging surface, a second end opposite to the first end, and a patient-specific length that is about equal to a thickness of the patient's articular cartilage at an area where the alignment guide is to be mounted, the patient-specific length is a custom length based on the thickness of the patient's articular cartilage measured from a multi-dimensional image of the patient's articular cartilage;
a patient-specific surface at the second end, the patient-specific surface configured to be complementary to and closely mate with an outer bone surface of the underlying bone, the patient-specific surface is a custom surface based on a multi-dimensional image of the patient's outer bone surface;
a bone anchoring portion extending from the second end; and
a shoulder between the second end and the bone-anchoring portion, the shoulder is patient-specific and customized to the patient based on a multi-dimensional image of the patient's outer bone surface, and configured to abut and closely mate with the outer surface of the underlying bone.

25. The orthopedic device of claim 24, wherein the alignment guide includes guiding bores for guiding alignment pins.

26. The orthopedic device of claim 24, wherein the inner anatomy-engaging surface is a three-dimensional patient-specific surface including a customized shape based on a multi-dimensional image of an outer cartilage surface of the bone of the patient and configured to nestingly mate to and be mounted on the outer cartilage surface of the bone of the patient in only one direction.

27. The orthopedic device of claim 24, wherein the bone anchoring portion includes a pointed tip for penetrating bone.

28. The orthopedic device of claim 24, wherein the bone anchoring portion has a smaller diameter than the cartilage anchoring portion.

* * * * *

UNITED STATES PATENT AND TRADEMARK OFFICE
CERTIFICATE OF CORRECTION

PATENT NO. : 8,864,769 B2  
APPLICATION NO. : 13/041495  
DATED : October 21, 2014  
INVENTOR(S) : Kevin T. Stone et al.

Page 1 of 1

It is certified that error appears in the above-identified patent and that said Letters Patent is hereby corrected as shown below:

In the Specification

Column 6, Line 26; Delete "103" and insert --83--.

Signed and Sealed this  
Seventh Day of April, 2015

Michelle K. Lee  
*Director of the United States Patent and Trademark Office*